(12) United States Patent
Isobe et al.

(10) Patent No.: US 10,858,677 B2
(45) Date of Patent: Dec. 8, 2020

(54) METHOD FOR PRODUCING 3-HYDROXYADIPIC ACID

(71) Applicant: TORAY INDUSTRIES, INC., Tokyo (JP)

(72) Inventors: Kyohei Isobe, Kamakura (JP); Kenji Kawamura, Kamakura (JP); Masateru Ito, Kamakura (JP); Katsushige Yamada, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 15/580,338

(22) PCT Filed: Jun. 9, 2016

(86) PCT No.: PCT/JP2016/067227
§ 371 (c)(1),
(2) Date: Dec. 7, 2017

(87) PCT Pub. No.: WO2016/199856
PCT Pub. Date: Dec. 15, 2016

(65) Prior Publication Data
US 2018/0142271 A1    May 24, 2018

(30) Foreign Application Priority Data

Jun. 10, 2015   (JP) .................................. 2015-117344

(51) Int. Cl.
| | | |
|---|---|---|
| C12P 7/44 | (2006.01) | |
| C12P 7/42 | (2006.01) | |
| C12N 1/20 | (2006.01) | |
| C12N 1/38 | (2006.01) | |

(52) U.S. Cl.
CPC .................. *C12P 7/44* (2013.01); *C12N 1/20* (2013.01); *C12N 1/38* (2013.01); *C12P 7/42* (2013.01)

(58) Field of Classification Search
None
See application file for complete search history.

(56) References Cited

U.S. PATENT DOCUMENTS

2011/0091944 A1*   4/2011   Wu ........................... C12P 7/44
                                                                435/121

FOREIGN PATENT DOCUMENTS

| EP | 3214072 A1 | 9/2017 |
|---|---|---|
| EP | 2265709 B1 | 11/2017 |
| JP | 2011-512868 A | 4/2011 |
| JP | 2011-515111 A | 5/2011 |
| WO | WO 2009/113853 A2 | 9/2009 |
| WO | WO 2014/043182 A2 | 3/2014 |
| WO | WO 2014/055649 A2 | 4/2014 |
| WO | WO 2016/068108 A1 | 6/2016 |

OTHER PUBLICATIONS

NBRC catalog entry for NBRC 12713, retrieved from http://www.nbrc.nite.go.jp/NBRC2/NBRCCatalogueDetailServlet?ID=NBRC& CAT=00012713 on Mar. 14, 2019 (Year: 2004).*
W, Ismail et al. "Functional genomics by NMR spectroscopy: Phenylacetate catabolism in *Escherichia coli*", European J. Biochemistry 270:3047-3054. (Year: 2003).*
P. John. "Aerobic and Anaerobic Bacterial Respiration Monitored by Electrodes", J. General Microbiology 98:231-238 (Year: 1977).*
Y.Kwon et al. "Long-term continuous adaptation of *Escherichia coli* to high succinate stress and transcriptome analysis of the tolerant strain", J. Bioscience Bioengineering 111(1):26-30 (Year: 2011).*
S. Sooan et al. "Acetate Consumption Activity Directly Determines the Level of Acetate Accumulation During *Escherichia coli* W3110 Growth", J. Microbiology Biotechnology 19(10: 1127-1134 (Year: 2009).*
Y. Li et al. "Proteomics analysis of aromatic catabolic pathways in thermophilic Geobacillus thermodenitrificans NG80-2", J. Proteomics 75:1201-1210 (Year: 2012).*
"NMR Sample Preparation", published by the Iowa State University Chemical Instrumentation Facility at https://www.cif.iastate.edu/sites/default/files/uploads/NMR/Manuals/NMR_Sample_Prep.pdf. (Year: 2013).*
"How to Prepare Samples for NMR" published by the University of Minnesota NMR Lab at http://nmr.chem.umn.edu/samprep.html (Year: 1999).*
"*E.coli* Metabolome Database" available at http://ecmdb.ca/ Home page, search of the term hydroxyadipic in the compound list, and prinout of the entries for (3S)-3-Hydroxyadipyl-CoA and 3-Hydroxyadipyl-CoA, retrieved on Mar. 13, 2020 (Year: 2020).*
Bird et al., "The Metabolism of n-Decane by a Pseudomonas," Biochem. J., vol. 104, 1967, pp. 987-990.
Harwood et al., "The β-Ketoadipate Pathway and the Biology of Self-Identity," Annu. Rev. Microbiol., vol. 50., 1996, pp. 553-590.

(Continued)

*Primary Examiner* — Rebecca E Prouty
(74) *Attorney, Agent, or Firm* — Birch, Stewart, Kolasch & Birch, LLP

(57) ABSTRACT

A novel method of producing 3-hydroxyadipic acid using a metabolic pathway of a microorganism is disclosed. The method of producing 3-hydroxyadipic acid includes the step of culturing at least one type of microorganism having a capacity to produce 3-hydroxyadipic acid, selected from the group consisting of microorganisms belonging to the genus *Escherichia*, microorganisms belonging to the genus *Pseudomonas*, microorganisms belonging to the genus *Hafnia*, microorganisms belonging to the genus *Corynebacterium*, microorganisms belonging to the genus *Bacillus*, microorganisms belonging to the genus *Streptomyces*, microorganisms belonging to the genus *Cupriavidus*, microorganisms belonging to the genus *Acinetobacter*, microorganisms belonging to the genus *Alcaligenes*, microorganisms belonging to the genus *Nocardioides*, microorganisms belonging to the genus *Brevibacterium*, microorganisms belonging to the genus *Delftia*, microorganisms belonging to the genus *Shimwellia*, microorganisms belonging to the genus *Aerobacter*, and microorganisms belonging to the genus *Rhizobium*.

3 Claims, No Drawings

(56) References Cited

OTHER PUBLICATIONS

Hyland, "Development of a Platform Strain for Production of Adipic Acid Yields Insights into the Localized Redox Metabolism of S. cerevisiae," Thesis—Master of Applied Science, Graduate Dept. of Chemical Engineering and Applied Chemistry, University of Toronto, 2013, pp, 1-47 (53 pages total).
International Search Report (Form PCT/ISA/210) for International Application No. PCT/JP2016/067227, dated Sep. 6, 2016.
Written Opinion of the Internationai Searching Authority (Form PCT/ISA/237) for International Application No. PCT/JP2016/067227, dated Sep. 6, 2016.
Extended European Search Report dated Dec. 20, 2018, in European Patent Application No. 16807562.0.
Hagen et al., "Engineering a Polyketide Synthase for In Vitro Production of Adipic Acid," ACS Synth. Biol. (2016), vol. 5, pp. 21-27.
Yuzawa et al., "Insights into polyketide biosynthesis gained from repurposing antibiotic-producing polyketide synthases to produce fuels and chemicals," The Journal of Antibiotics (2016), vol. 69, pp. 494-499.

\* cited by examiner

METHOD FOR PRODUCING 3-HYDROXYADIPIC ACID

TECHNICAL FIELD

The present invention relates to a method of producing 3-hydroxyadipic acid using a microorganism.

BACKGROUND ART

3-Hydroxyadipic acid (IUPAC name: 3-hydroxyhexanedioic acid) is a dicarboxylic acid having a carbon number of 6 and a molecular weight of 162.14. 3-Hydroxyadipic acid can be used as a raw material for polyesters by polymerization with a polyol, or for polyamides by polymerization with a polyamine. By lactamizing 3-hydroxyadipic acid by addition of ammonia to its terminus, it can also be used as a raw material for polyamides by itself.

As a report related to a method of producing 3-hydroxyadipic acid using a microorganism, there is a report disclosing that, during a method of producing adipic acid using succinyl-CoA and acetyl-CoA as starting materials and a non-naturally occurring microorganism, 3-oxoadipic acid (3-oxoadipate) as an intermediate in an adipic acid biosynthetic pathway is reduced by an enzymatic reaction (3-oxoadipate reductase) to allow production of 3-hydroxyadipic acid (Patent Document 1, FIG. 3). Production of a very small amount of 3-hydroxyadipic acid (β-hydroxyadipic acid) by metabolism of n-decane in *Pseudomonas* X2 has also been reported (Non-patent Document 1).

PRIOR ART DOCUMENTS

Patent Document

[Patent Document 1] WO 2009/151728

Non-Patent Document

[Non-patent Document 1] Biochem. J. 1967 104, 987-990

SUMMARY OF THE INVENTION

Problems to be Solved by the Invention

Patent Document 1 describes that, in a microorganism which is artificially modified such that adipic acid can be produced, 3-oxoadipic acid (3-oxoadipate) as an intermediate of adipic acid, which is the product of interest, is reduced by an enzymatic reaction to allow production of 3-hydroxyadipic acid (3-hydroxyadipate). However, no direct evidence for the reduction reaction from 3-oxoadipic acid to 3-hydroxyadipic acid by 3-oxoadipate reductase has been found, and no test has been carried out for confirming whether 3-hydroxyadipic acid can be actually produced using a metabolic pathway in a microorganism. Moreover, since the enzyme 3-oxoadipate reductase is not well known to those skilled in the art, production of 3-hydroxyadipic acid using succinyl-CoA and acetyl-CoA as starting materials according to the description in Patent Document 1 has been impossible.

Although Non-patent Document 1 reports that 3-hydroxyadipic acid is produced by *Pseudomonas* X2, the productivity is so low that only a small amount of the product is detected by NMR. The method cannot therefore be said to be a method of producing 3-hydroxyadipic acid.

Thus, there has practically been no method of producing 3-hydroxyadipic acid using a metabolic pathway of a microorganism. In view of this, the present invention aims to provide a method of producing 3-hydroxyadipic acid using a metabolic pathway in a microorganism.

Means for Solving the Problems

As a result of intensive study for solving the above problem, the present inventors discovered that a microorganism capable of producing 3-hydroxyadipic acid using a metabolic pathway exists in nature, to reach the present invention.

That is, the present invention provides the following (1) to (19).

(1) A method of producing 3-hydroxyadipic acid, the method comprising the step of culturing at least one type of microorganism having a capacity to produce 3-hydroxyadipic acid, selected from the group consisting of microorganisms belonging to the genus *Escherichia*, microorganisms belonging to the genus *Pseudomonas*, microorganisms belonging to the genus *Hafnia*, microorganisms belonging to the genus *Corynebacterium*, microorganisms belonging to the genus *Bacillus*, microorganisms belonging to the genus *Streptomyces*, microorganisms belonging to the genus *Cupriavidus*, microorganisms belonging to the genus *Acinetobacter*, microorganisms belonging to the genus *Alcaligenes*, microorganisms belonging to the genus *Nocardioides*, microorganisms belonging to the genus *Brevibacterium*, microorganisms belonging to the genus *Delftia*, microorganisms belonging to the genus *Shimwellia*, microorganisms belonging to the genus *Aerobacter*, and microorganisms belonging to the genus *Rhizobium*.

(2) The method according to (1), wherein the microorganism is at least one selected from the group consisting of microorganisms belonging to the genus *Cupriavidus*, microorganisms belonging to the genus *Acinetobacter*, microorganisms belonging to the genus *Delftia*, microorganisms belonging to the genus *Shimwellia*, microorganisms belonging to the genus *Escherichia*, and microorganisms belonging to the genus *Pseudomonas*.

(3) The method according to (1) or (2), wherein the microorganism belonging to the genus *Escherichia* is *Escherichia fergusonii* or *Escherichia coli*.

(4) The method according to (1) or (2), wherein the microorganism belonging to the genus *Pseudomonas* is *Pseudomonas chlororaphis*, *Pseudomonas putida*, *Pseudomonas azotoformans*, or *Pseudomonas chlororaphis* subsp. *aureofaciens*.

(5) The method according to (1), wherein the microorganism belonging to the genus *Hafnia* is *Hafnia alvei*.

(6) The method according to (1), wherein the microorganism belonging to the genus *Corynebacterium* is *Corynebacterium acetoacidophilum*, *Corynebacterium acetoglutamicum*, *Corynebacterium ammoniagenes*, or *Corynebacterium glutamicum*.

(7) The method according to (1), wherein the microorganism belonging to the genus *Bacillus* is *Bacillus badius*, *Bacillus magaterium*, or *Bacillus roseus*.

(8) The method according to (1), wherein the microorganism belonging to the genus *Streptomyces* is *Streptomyces vinaceus*, *Streptomyces karnatakensis*, or *Streptomyces olivaceus*.

(9) The method according to (1) or (2), wherein the microorganism belonging to the genus *Cupriavidus* is *Cupriavidus metallidurans*, *Cupriavidus necator*, or *Cupriavidus oxalaticus*.

(10) The method according to (1) or (2), wherein the microorganism belonging to the genus *Acinetobacter* is *Acinetobacter baylyi* or *Acinetobacter radioresistens*.
(11) The method according to (1) or (2), wherein the microorganism belonging to the genus *Alcaligenes* is *Alcaligenes faecalis*.
(12) The method according to (1), wherein the microorganism belonging to the genus *Nocardioides* is *Nocardioides albus*.
(13) The method according to (1), wherein the microorganism belonging to the genus *Brevibacterium* is *Brevibacterium iodinum*.
(14) The method according to (1) or (2), wherein the microorganism belonging to the genus *Delftia* is *Delftia acidovorans*.
(15) The method according to (1) or (2), wherein the microorganism belonging to the genus *Shimwellia* is *Shimwellia blattae*.
(16) The method according to (1), wherein the microorganism belonging to the genus *Aerobacter* is *Aerobacter cloacae*.
(17) The method according to (1), wherein the microorganism belonging to the genus *Rhizobium* is *Rhizobium radiobacter*.
(18) The method according to any one of (1) to (17), wherein a medium with which the microorganism is cultured contains at least one carbon source selected from the group consisting of saccharides, succinic acid, 2-oxoglutaric acid, and glycerol.
(19) The method according to any one of (1) to (18), wherein the microorganism is cultured with a medium containing at least one inducer selected from the group consisting of ferulic acid, p-coumaric acid, benzoic acid, cis,cis-muconic acid, protocatechuic acid, and catechol.

Effect of the Invention

By the present invention, 3-hydroxyadipic acid can be produced using a metabolic pathway of a microorganism.

Mode for Carrying Out the Invention

The method of producing 3-hydroxyadipic acid of the present invention comprises the step of culturing a microorganism having a capacity to produce 3-hydroxyadipic acid. More specifically, the present invention is characterized in that 3-hydroxyadipic acid is produced using a metabolic pathway of a microorganism having a capacity to produce 3-hydroxyadipic acid, by culturing the microorganism.

The microorganism having a capacity to produce 3-hydroxyadipic acid used in the method of the present invention is selected from the following microorganisms.
Microorganisms belonging to the genus *Cupriavidus*
Microorganisms belonging to the genus *Acinetobacter*
Microorganisms belonging to the genus *Delftia*
Microorganisms belonging to the genus *Shimwellia*
Microorganisms belonging to the genus *Escherichia*
Microorganisms belonging to the genus *Pseudomonas*
Microorganisms belonging to the genus *Aerobacter*
Microorganisms belonging to the genus *Alcaligenes*
Microorganisms belonging to the genus *Bacillus*
Microorganisms belonging to the genus *Brevibacterium*
Microorganisms belonging to the genus *Corynebacterium*
Microorganisms belonging to the genus *Hafnia*
Microorganisms belonging to the genus *Nocardioides*
Microorganisms belonging to the genus *Rhizobium*
Microorganisms belonging to the genus *Streptomyces*.

Specific examples of microorganisms having a capacity to produce 3-hydroxyadipic acid and belonging to the genus *Cupriavidus* include *Cupriavidus metallidurans*, *Cupriavidus necator*, and *Cupriavidus oxalaticus*. The mechanism by which microorganisms belonging to the genus *Cupriavidus* can produce 3-hydroxyadipic acid using their metabolic pathway is not clear. Since the genus *Capriavidus* is known to degrade hydrocarbons derived from petroleum products such as benzene, toluene, and xylene (see JP 2007-252285 A), and to have metal tolerance (Antonie van Leeuwenhoek, 2009, 96, 2, 115-139), it is assumed that microorganisms belonging to the genus *Capriavidus* have a complex metabolic pathway which is different from those of microorganisms commonly used for matter production, and that they produce 3-hydroxyadipic acid based on this metabolic pathway.

Specific examples of microorganisms having a capacity to produce 3-hydroxyadipic acid and belonging to the genus *Acinetobacter* include *Acinetobacter baylyi* and *Acinetobacter radioresistens*. The mechanism by which microorganisms belonging to the genus *Acinetobacter* can produce 3-hydroxyadipic acid using their metabolic pathway is also not clear. Since the genus *Acinetobacter* is known to degrade mineral oils such as benzene, fuel oils, and lubricating oils, and hence to be applicable to environmental cleanup (see JP 2013-123418 A), it is assumed that microorganisms belonging to the genus *Acinetobacter* have a complex metabolic pathway which is different from those of microorganisms commonly used for matter production, and that they produce 3-hydroxyadipic acid based on this metabolic pathway, similarly to the genus *Capriavidus*.

Specific examples of microorganisms having a capacity to produce 3-hydroxyadipic acid and belonging to the genus *Delftia* include *Delftia acidovorans*. The mechanism by which microorganisms belonging to the genus *Delftia* can produce 3-hydroxyadipic acid using their metabolic pathway is also not clear. Since the genus *Delftia* is known to degrade mineral oils such as benzene, fuel oils, and lubricating oils, and hence to be applicable to environmental cleanup (see JP 2013-123418 A), and to have metal tolerance (Journal of Water Resource and Protection, 2012, 4, 4, 207-216), it is assumed that microorganisms belonging to the genus *Delftia* have a complex metabolic pathway which is different from those of microorganisms commonly used for matter production, and that they produce 3-hydroxyadipic acid based on this metabolic pathway, similarly to the genus *Capriavidus* and the genus *Acinetobacter*.

Specific examples of microorganisms having a capacity to produce 3-hydroxyadipic acid and belonging to the genus *Shimwellia* include *Shimwellia blattae*. The mechanism by which microorganisms belonging to the genus *Shimwellia* can produce 3-hydroxyadipic acid using their metabolic pathway is also not clear. Since the genus *Shimwellia* is known to also inhabit a place where a radioactive radon concentration is high (see Radiation Protection and Environment, 2014, 37, 1, 21-24), it is assumed that microorganisms belonging to the genus *Shimwellia* have a complex metabolic pathway which is different from those of microorganisms commonly used for matter production, and that they produce 3-hydroxyadipic acid based on this metabolic pathway, similarly to the genus *Capriavidus*, the genus *Acinetobacter*, and the genus *Delftia*.

Specific examples of microorganisms having a capacity to produce 3-hydroxyadipic acid and belonging to the genus

*Escherichia* include *Escherichia fergusonii* and *Escherichia coli*. The mechanism by which microorganisms belonging to the genus *Escherichia* can produce 3-hydroxyadipic acid using their metabolic pathway is also not clear. Since the genus *Escherichia* is known to have a hydrocarbon-degrading capacity and heavy metal tolerance (see Bioresource Technology, 2011, 102, 19, 9291-9295), it is assumed that microorganisms belonging to the genus *Escherichia* have a complex metabolic pathway which is different from those of microorganisms commonly used for matter production (for example, microorganisms belonging to the genus *Corynebacterium*), and that they produce 3-hydroxyadipic acid based on this metabolic pathway, similarly to the genus *Capriavidus*, the genus *Acinetobacter*, the genus *Delftia*, and the genus *Shimwellia*.

Specific examples of microorganisms having a capacity to produce 3-hydroxyadipic acid and belonging to the genus *Pseudomonas* include *Pseudomonas chlororaphis*, *Pseudomonas putida*, *Pseudomonas azotoformans*, and *Pseudomonas chlororaphis* subsp. *aureofaciens*. The mechanism by which microorganisms belonging to the genus *Pseudomonas* can produce 3-hydroxyadipic acid using their metabolic pathway is also not clear. Since the genus *Pseudomonas* is known to degrade aromatic hydrocarbon-based solvents, petroleum hydrocarbon-based solvents, ester-based solvents, alcohol-based solvents, and the like (see JP 2010-130950 A), it is assumed that microorganisms belonging to the genus *Pseudomonas* have a complex metabolic pathway which is different from those of microorganisms commonly used for matter production (for example, microorganisms belonging to the genus *Corynebacterium*), and that they produce 3-hydroxyadipic acid based on this metabolic pathway, similarly to the genus *Capriavidus*, the genus *Acinetobacter*, the genus *Delftia*, the genus *Shimwellia*, and the genus *Escherichia*.

Specific examples of microorganisms having a capacity to produce 3-hydroxyadipic acid and belonging to the genus *Aerobacter* include *Aerobacter cloacae*. The mechanism by which microorganisms belonging to the genus *Aerobacter* can produce 3-hydroxyadipic acid using their metabolic pathway is also not clear. Since the genus *Aerobacter* is known to degrade a pesticide DDT (1,1,1-trichloro-2-bis(p-chlorophenyl)ethane) (see New Zealand Journal of Agricultural Research, Volume 40, Issue 2, 1997), it is assumed that they have a complex metabolic pathway which is different from those of microorganisms commonly used for matter production, and that they produce 3-hydroxyadipic acid based on this metabolic pathway.

Specific examples of microorganisms having a capacity to produce 3-hydroxyadipic acid and belonging to the genus *Alcaligenes* include *Alcaligenes faecalis*. The mechanism by which microorganisms belonging to the genus *Alcaligenes* can produce 3-hydroxyadipic acid using their metabolic pathway is also not clear. Since the genus *Alcaligenes* is used for purification of phenol compound-containing wastewater (see, JP 2016-41392 A), it is assumed that they have a complex metabolic pathway which is different from those of microorganisms commonly used for matter production, and that they produce 3-hydroxyadipic acid based on this metabolic pathway.

Specific examples of microorganisms having a capacity to produce 3-hydroxyadipic acid and belonging to the genus *Bacillus* include *Bacillus badius, Bacillus magaterium*, and *Bacillus roseus*. The mechanism by which microorganisms belonging to the genus *Bacillus* can produce 3-hydroxyadipic acid using their metabolic pathway is also not clear. Since the genus *Bacillus* is used for wastewater processing systems in which wastewater is biologically treated with activated sludge (see JP 2006-305455 A), it is assumed that they have a complex metabolic pathway which is different from those of microorganisms commonly used for matter production, and that they produce 3-hydroxyadipic acid based on this metabolic pathway.

Specific examples of microorganisms having a capacity to produce 3-hydroxyadipic acid and belonging to the genus *Brevibacterium* include *Brevibacterium iodinum*. The mechanism by which microorganisms belonging to the genus *Brevibacterium* can produce 3-hydroxyadipic acid using their metabolic pathway is also not clear. Since the genus *Brevibacterium* is known to degrade ochratoxin A, which is a toxin produced by a mold (see J. Agric. Food Chem., 2011, 59 (19), pp 10755-10760), it is assumed that they have a complex metabolic pathway which is different from those of microorganisms commonly used for matter production, and that they produce 3-hydroxyadipic acid based on this metabolic pathway.

Specific examples of microorganisms having a capacity to produce 3-hydroxyadipic acid and belonging to the genus *Corynebacterium* include *Corynebacterium acetoacidophilum, Corynebacterium acetoglutamicum, Corynebacterium ammoniagenes*, and *Corynebacterium glutamicum*. The mechanism by which microorganisms belonging to the genus *Corynebacterium* can produce 3-hydroxyadipic acid using their metabolic pathway is also not clear. Since the genus *Corynebacterium* is known to have a capacity to degrade polycyclic aromatic hydrocarbons (see Prevalence of polycyclic aromatic hydrocarbons (PAHs) degrading bacteria in contaminated tropical soil in Lagos, Nigeria: involvement of plasmid in degradation., International Journal of Biological and Chemical Sciences 2010 Vol. 4 No. 6 pp. unpaginated), it is assumed that they have a complex metabolic pathway which is different from those of microorganisms commonly used for matter production, and that they produce 3-hydroxyadipic acid based on this metabolic pathway.

Specific examples of microorganisms having a capacity to produce 3-hydroxyadipic acid and belonging to the genus *Hafnia* include *Hafnia alvei*. The mechanism by which microorganisms belonging to the genus *Hafnia* can produce 3-hydroxyadipic acid using their metabolic pathway is also not clear. Since the genus *Hafnia* is known to be tolerant to chromic acid contained in wastewater, and to degrade it (see J. bio-sci. 17: 71-76, 2009), it is assumed that they have a complex metabolic pathway which is different from those of microorganisms commonly used for matter production, and that they produce 3-hydroxyadipic acid based on this metabolic pathway.

Specific examples of microorganisms having a capacity to produce 3-hydroxyadipic acid and belonging to the genus *Nocardioides* include *Nocardioides albus*. The mechanism by which microorganisms belonging to the genus *Nocardioides* can produce 3-hydroxyadipic acid using their metabolic pathway is also not clear. Since the genus *Nocardioides* is known to degrade petroleum (see Isolation and Identification of Petroleum-Degradable Bacterial Strain and Its Oil-Degradation Characteristics, Journal of Microbiology, 2012-05), it is assumed that they have a complex metabolic pathway which is different from those of microorganisms commonly used for matter production, and that they produce 3-hydroxyadipic acid based on this metabolic pathway.

Specific examples of microorganisms having a capacity to produce 3-hydroxyadipic acid and belonging to the genus *Rhizobium* include *Rhizobium radiobacter*. The mechanism by which microorganisms belonging to the genus *Rhizobium* can produce 3-hydroxyadipic acid using their metabolic pathway is also not clear. Since the genus *Rhizobium* is known to degrade a dye methyl violet (see Journal of Basic Microbiology, Volume 49, Issue Supplement S1 September 2009 Pages S36-S42), it is assumed that they have a complex metabolic pathway which is different from those of microorganisms commonly used for matter production, and that they produce 3-hydroxyadipic acid based on this metabolic pathway.

Specific examples of microorganisms having a capacity to produce 3-hydroxyadipic acid and belonging to the genus *Streptomyces* include *Streptomyces vinaceus, Streptomyces karnatakensis,* and *Streptomyces olivaceus*. The mechanism by which microorganisms belonging to the genus *Streptomyces* can produce 3-hydroxyadipic acid using their metabolic pathway is also not clear. Since the genus *Streptomyces* is known to produce various antibiotics (see Tetrahedron Volume 39, Issue 15, 1983, Pages 2551-2562), it is assumed that they have a complex metabolic pathway which is different from those of microorganisms commonly used for matter production, and that they produce 3-hydroxyadipic acid based on this metabolic pathway. All of the microorganisms described above are known as microorganisms present in nature, and can be isolated from natural environments such as soils. They can also be purchased from microorganism-distributing agencies such as ATCC.

The microorganism may be one prepared by recombination of a gene(s) according to a known method, or one prepared by mutation of a gene(s) by artificial mutation means, as long as the microorganism produces 3-hydroxyadipic acid.

The fact that the microorganism has a capacity to produce 3-hydroxyadipic acid can be confirmed by subjecting the supernatant of the culture liquid to an appropriate analysis method such as high-performance liquid chromatography (HPLC), high-performance liquid chromatography-mass spectrometry (LC/MS), high-performance liquid chromatography-tandem mass spectrometry (LC-MS/MS), gas chromatography (GC), or gas chromatography-mass spectrometry (GC/MS), to detect 3-hydroxyadipic acid contained in the culture supernatant. In the present invention, it is preferred to use, as the microorganism having a capacity to produce 3-hydroxyadipic acid, a microorganism capable of producing not less than 1.0 mg/L of 3-hydroxyadipic acid in a culture supernatant obtained by culturing the microorganism for 20 hours to 48 hours.

In the method of the present invention, each of the microorganisms described above is cultured under conditions where 3-hydroxyadipic acid is produced. In the present invention, the microorganism is cultured in a medium suitable for the microorganism used, for example, in a medium, preferably a liquid medium, containing a carbon source that can be metabolized by ordinary microorganisms. Here, the "metabolism" in the present invention means that a chemical substance which is incorporated from the outside of the cell or generated from another chemical substance in the cell by a microorganism is converted to another chemical substance by enzymatic reaction. In cases where the microorganism is grown by culture, the medium preferably contains a carbon source assimilable by the microorganism cultured.

The medium used contains, besides the carbon source metabolizable by the microorganism used, suitable amounts of a metabolizable (preferably assimilable) nitrogen source, inorganic salt, and, if necessary, an organic micronutrient such as amino acid or vitamin. As long as the above nutrient sources are contained, the medium used may be either a natural medium or synthetic medium.

As the carbon source metabolizable by the microorganism, saccharides may be preferably used. Besides saccharides, any carbon source may be preferably used as long as it can be used as a sole carbon source for the growth of the microorganism. Specific examples of preferred carbon sources include monosaccharides such as glucose, sucrose, fructose, galactose, mannose, xylose, and arabinose; disaccharides and polysaccharides containing these monosaccharides bound to each other; starch saccharified liquids, molasses, and cellulose-containing biomass saccharified liquids containing these saccharides; organic acids such as acetic acid, succinic acid, lactic acid, fumaric acid, citric acid, propionic acid, malic acid, malonic acid, adipic acid, 2-oxoglutaric acid, and pyruvic acid; monovalent alcohols such as methanol, ethanol, and propanol; polyols such as glycerin, ethylene glycol, and propanediol; hydrocarbons; fatty acids; and oils. The carbon sources described above may be used either individually or in combination. More specifically, the microorganism can efficiently produce 3-hydroxyadipic acid by metabolizing, among these carbon sources, one or more selected from the group consisting of saccharides, succinic acid, 2-oxoglutaric acid, and glycerol. The concentration of the saccharide(s) in the medium is not limited, and may be appropriately selected depending on the type of the microorganism cultured, the type(s) of the saccharide(s), and/or the like. The concentration is usually about 5 g/L to 300 g/L.

Examples of the assimilable nitrogen source used for the culture of the microorganism include ammonia gas, aqueous ammonia, ammonium salts, urea, nitrates, and other supplementary organic nitrogen sources, for example, oil cakes, soybean hydrolysates, casein digests, other amino acids, vitamins, corn steep liquor, yeasts or yeast extracts, meat extracts, peptides such as peptone, and various fermentation microorganism cells and hydrolysates thereof. The concentration of the nitrogen source in the medium is not limited, and may be appropriately selected depending on the type of the microorganism cultured, the type of the nitrogen source, and/or the like. The concentration is usually about 0.1g/L to 50 g/L.

Examples of inorganic salts which may be added as appropriate to be used for the culture of the microorganism include phosphoric acid salts, magnesium salts, calcium salts, iron salts, and manganese salts.

Conditions of the culture of the microorganism to be set for the production of 3-hydroxyadipic acid, such as the medium having the component composition described above, culture temperature, stirring rate, pH, aeration rate, and inoculation amount, may be appropriately controlled or selected based on the type of the production microorganism used, external conditions, and/or the like. In cases where foaming occurs in the liquid culture, an antifoaming agent such a mineral oil, silicone oil, or surfactant may be included as appropriate in the medium. These culture conditions are known for each microorganism, and also specifically described in the following Examples.

By the medium and the culture conditions described above, 3-hydroxyadipic acid can be produced by culture using the microorganism. More efficient production of 3-hydroxyadipic acid is possible by culturing the microorganism in a state where a metabolic pathway required for the production of 3-hydroxyadipic acid is activated. The method of activating the metabolic pathway is not limited, and examples of the method include a method in which the microorganism is cultured in a medium containing a substance that activates a metabolic pathway(s) (hereinafter also referred to as inducer) to induce expression of an enzyme gene(s) in a metabolic pathway(s) for the production of 3-hydroxyadipic acid, a method in which a coding region(s) of an enzyme gene(s) and/or a functional region(s) in the vicinity thereof is/are modified by a gene modification technique, a method in which the copy number(s) of an enzyme gene(s) is/are increased, and a method in which an enzyme gene function(s) in a biosynthetic pathway(s) of a by-product(s) is/are destroyed. The method is preferably a method in which expression of an enzyme gene(s) in a metabolic pathway(s) for the production of 3-hydroxyadipic acid is induced by an inducer(s).

The inducer is not limited as long as it is a substance that activates a metabolic pathway required for the production of 3-hydroxyadipic acid. Examples of the inducers which may be usually used include aromatic compounds, and aliphatic compounds having a carbon number of not less than 6, preferably 6 to 30, which are metabolized into compounds having smaller carbon numbers through 3-oxoadipyl-CoA as an intermediate. The aliphatic compound having a carbon number of not less than 6 is preferably a dicarboxylic acid having a carbon number of not less than 6, preferably 6 to 30. Examples of such a compound can be known using a database such as KEGG (Kyoto Encyclopedia of Genes and Genomes). Specific examples of the compound include adipic acid, benzoic acid, cis,cis-muconic acid, terephthalic acid, protocatechuic acid, catechol, vanillin, coumaric acid, and ferulic acid. Preferred examples of the compound include adipic acid, ferulic acid, and p-coumaric acid.

The above inducers may be used either individually or in combination of two or more thereof depending on the microorganism used for the production of 3-hydroxyadipic acid. The inducer may be contained in the medium used in culture for growing the microorganism (preculture) in a stage preceding the production of 3-hydroxyadipic acid, or may be contained in the medium used for the production of 3-hydroxyadipic acid. In cases where one or more inducers are contained in the medium, the concentration of the inducer(s) (total concentration in cases where a plurality of inducers are contained) is not limited, and appropriately selected depending on the type of the microorganism, type (s) of the inducer(s), and the like. The concentration is usually 1 mg/L to 10 g/L, preferably 5 mg/L to 1 g/L.

After allowing production of 3-hydroxyadipic acid in the culture of the microorganism to an amount at which 3-hydroxyadipic acid can be recovered, the 3-hydroxyadipic acid produced can be recovered. The recovery, for example, isolation, of the 3-hydroxyadipic acid produced can be carried out according to a general method in which the culture is stopped at a time point when accumulation of the product proceeded to an appropriate level, and then a fermentation product is collected from the culture. More specifically, after separating microbial cells by centrifugation, filtration, and/or the like, 3-hydroxyadipic acid can be isolated from the culture by column chromatography, ion-exchange chromatography, activated carbon treatment, crystallization, membrane separation, distillation, and/or the like. Still more specifically, preferred examples of the recovering method include, but are not limited to, a method in which the culture is subjected to removal of water by a concentration operation using a reverse osmosis membrane, evaporator, and/or the like to increase the concentration of 3-hydroxyadipic acid, and crystals of 3-hydroxyadipic acid and/or a salt of 3-hydroxyadipic acid are precipitated by cooling crystallization or insulated crystallization, followed by obtaining crystals of 3-hydroxyadipic acid and/or the salt of 3-hydroxyadipic acid by centrifugation, filtration, and/or the like, and a method in which alcohol is added to the culture to produce 3-hydroxyadipic acid ester, and then the 3-hydroxyadipic acid ester is recovered by a distillation operation, followed by performing hydrolysis to obtain 3-hydroxyadipic acid.

EXAMPLES

The present invention is described below concretely by way of Examples. However, the present invention is not limited to these.

Reference Example 1

Preparation of 3-Hydroxyadipic Acid

The 3-hydroxyadipic acid used in the analysis in the Examples described below was prepared by chemical synthesis.

First, 1.5 L of super-dehydrated tetrahydrofuran (manufactured by Wako Pure Chemical Industries, Ltd.) was added to 13.2 g (0.1 mol) of succinic acid monomethyl ester (manufactured by Wako Pure Chemical Industries, Ltd.), and 16.2 g (0.1 mol) of carbonyldiimidazole (manufactured by Wako Pure Chemical Industries, Ltd.) was added thereto with stirring, followed by stirring the resulting mixture under nitrogen atmosphere for 1 hour at room temperature. To this suspension, 15.6 g (0.1 mol) of malonic acid monomethyl ester potassium salt and 9.5 g (0.1 mol) of magnesium chloride were added. The resulting mixture was stirred under nitrogen atmosphere for 1 hour at room temperature, and then stirred at 40° C. for 12 hours. After the reaction, 0.05 L of 1 mol/L hydrochloric acid was added to the mixture, and extraction with ethyl acetate was carried out. By separation purification by silica gel column chromatography (hexane:ethyl acetate=1:5), 13.1 g of pure 3-oxohexanedicarboxylic acid dimethyl ester was obtained. Yield: 70%.

To 10 g (0.05 mol) of the 3-oxohexanedicarboxylic acid dimethyl ester obtained, 0.1 L of methanol (manufactured by Kokusan Chemical Co., Ltd.) was added, and 0.02 L of 5 mol/L aqueous sodium hydroxide solution was added to the resulting mixture with stirring, followed by stirring the mixture at room temperature for 2 hours. After the reaction, the pH was adjusted to 1 with 5 mol/L hydrochloric acid. Subsequently, 2.0 g (0.05 mol) of sodium borohydride (manufactured by Wako Pure Chemical Industries, Ltd.) was added thereto, and the resulting mixture was stirred at room temperature for 2 hours. After the reaction, the mixture was concentrated using a rotary evaporator. By recrystallization with water, 7.2 g of pure 3-hydroxyadipic acid was obtained. Yield: 95%.

$^1$H-NMR spectrum of 3-hydroxyadipic acid:
$^1$H-NMR (400 MHz, CD3OD): δ1.70 (m, 1H), δ1.83 (m, 1H), δ2.42 (m, 4H), δ4.01 (m, 1H).

Example 1

3-Hydroxyadipic Acid Production Test Using Succinic Acid Microbial Culture

The 3-hydroxyadipic acid productivities of the microorganisms shown in Table 1 (all microorganisms were purchased from microorganism-distributing agencies; the distributors are described in the strain names) were investigated. To 5 mL of a medium containing 10 g/L tryptone, 5 g/L yeast extract, 5 g/L sodium chloride, and 0.5 g/L adipic acid (pH 7), a loopful of each microorganism was inoculated, and shake culture was carried out at 30° C. until the microorganism was sufficiently suspended (preculture). To the culture liquid, 10 mL of 0.9% sodium chloride was added, and the microbial cells were centrifuged, followed by completely removing the supernatant, thereby washing the microbial cells. After carrying out this operation three times, the microbial cells were suspended in 1 mL of 0.9% sodium chloride. To 5 mL of the medium having the following composition containing succinic acid as a carbon source, 0.5 mL of the resulting suspension was added, and shake culture was performed at 30° C. for 20 hours (main culture). The main culture liquid was subjected to centrifugation to separate microbial cells, and the resulting supernatant was analyzed by LC-MS/MS.

Medium Composition for the Main Culture:
20 g/L succinic acid
2 g/L ammonium sulfate
100 mM potassium phosphate
0.05 g/L magnesium sulfate
0.125 mg/L iron sulfate
5.4 mg/L manganese sulfate
0.66 mg/L calcium chloride
0.25 g/L yeast extract
pH 6.5.

Quantitative Analysis of 3-Hydroxyadipic Acid

Quantitative analysis of 3-hydroxyadipic acid by LC-MS/MS was carried out under the following conditions.
HPLC: 1290 Infinity (manufactured by Agilent Technologies)
Column: Synergi hydro-RP (manufactured by Phenomenex); length, 100 mm; inner diameter, 3 mm; particle size, 2.5 μm
Mobile phase: 0.1% aqueous formic acid solution/methanol=70/30
Flow rate: 0.3 mL/minute
Column temperature: 40° C.
LC detector: DAD (210 nm)
MS/MS: Triple-Quad LC/MS (manufactured by Agilent Technologies)
Ionization method: ESI negative mode.

The concentration of 3-hydroxyadipic acid accumulated in the culture supernatant was as shown in Table 1. It was confirmed that all microorganisms have a capacity to produce 3-hydroxyadipic acid.

TABLE 1

| Test microorganism | 3-Hydroxyadipic acid (mg/L) |
|---|---|
| Cupriavidus metallidurans NBRC101272 | 19 |
| Cupriavidus necator NBRC102504 | 1.5 |
| Cupriavidus oxalaticus NBRC13593 | 1.4 |
| Cupriavidus sp. NBRC102508 | 6.6 |
| Acinetobacter baylyi ATCC33305 | 1.2 |
| Acinetobacter sp. NBRC100985 | 1.5 |
| Delftia acidovorans ATCC11299 | 2.7 |
| Shimwellia blattae NBRC105725 | 2.0 |
| Escherichia fergusonii NBRC102419 | 1.0 |
| Escherichia coli NBRC12713 | 1.1 |
| Pseudomonas chlororaphis ATCC13985 | 1.4 |
| Pseudomonas putida ATCC8209 | 2.6 |
| Pseudomonas sp. ATCC15915 | 2.5 |

Example 2

Production Example of 3-Hydroxyadipic Acid

To 5 mL of LB medium, a loopful of Cupriavidus metallidurans NBRC101272, which was confirmed to be a microorganism having a capacity to produce 3-hydroxyadipic acid in Example 1, was inoculated, and shake culture was carried out at 30° C. until the microorganism was sufficiently suspended (pre-preculture). To 100 mL of a medium containing 10 g/L tryptone, 5 g/L yeast extract, 5 g/L sodium chloride, and 0.5 g/L adipic acid (pH 7), 2 mL of the pre-preculture liquid was added, and shake culture was carried out at 30° C. until the microorganism was sufficiently suspended (preculture). After removing the preculture liquid by washing with 200 mL of 0.9% sodium chloride three times in the same manner as in Example 1, the microbial cells were suspended in 10 mL of 0.9% sodium chloride. To 100 mL of the same main culture medium containing succinic acid as a carbon source as in Example 1, 10 mL of the resulting suspension was added, and shake culture was performed at 30° C. for 20 hours (main culture). The main culture liquid was subjected to centrifugation to separate microbial cells, and the resulting supernatant was analyzed by LC-MS/MS in the same manner as in Example 1. As a result, the concentration of 3-hydroxyadipic acid accumulated in the culture supernatant was found to be 18 mg/L.

Subsequently, the supernatant from the main culture was concentrated under reduced pressure, to obtain 11 mL of a concentrate having a 3-hydroxyadipic acid concentration of 160 mg/L. The resulting concentrate was injected into HPLC to which a fraction collection device was connected, and a fraction having the same elution time as a 3-hydroxyadipic acid sample was collected. This operation was carried out ten times for removal of impurities in the culture liquid, to obtain an aqueous 3-hydroxyadipic acid solution. The preparative HPLC used for the collection of 3-hydroxyadipic acid was carried out under the following conditions.

HPLC: SHIMADZU 20A (manufactured by Shimadzu Corporation)
Column: Synergi hydro-RP (manufactured by Phenomenex); length, 250 mm; inner diameter, 10 mm; particle size, 4μm
Mobile phase: 5 mM aqueous formic acid solution/acetonitrile=98/2
Flow rate: 4 mL/minute
Injection volume: 1 mL
Column temperature: 45° C.
Detector: UV-VIS (210 nm)
Fraction collection device: FC204 (manufactured by Gilson)

Subsequently, the aqueous 3-hydroxyadipic acid solution was concentrated under reduced pressure, to obtain 1.4 mg of crystals. As a result of analysis of the crystals by $^1$H-NMR, the obtained crystals was confirmed to be 3-hydroxyadipic acid.

Comparative Example 1

Microorganism Having No Capacity to Produce 3-Hydroxyadipic Acid

In order to investigate the 3-hydroxyadipic acid productivity of the microorganism shown in Table 2, microbial culture was carried out under the same conditions as in Example 1, and quantitative analysis of 3-hydroxyadipic acid was carried out. As a result, no 3-hydroxyadipic acid was detected in the culture supernatant.

TABLE 2

| Test microorganism | 3-Hydroxyadipic acid (mg/L) |
|---|---|
| *Zymomonas mobilis* NBRC13756 | N.D. |

Comparative Example 2

Culture without Addition of Carbon Source

The microorganisms shown in Table 1 were cultured under the same conditions as in Example 1 except that a medium having a composition containing no succinic acid was used. As a result of quantitative analysis of 3-hydroxyadipic acid, no 3-hydroxyadipic acid was detected in the culture supernatant. From this result, it was confirmed that the 3-hydroxyadipic acid quantified in Example 1 was produced as a result of metabolism of succinic acid by the microorganism.

Example 3

3-Hydroxyadipic Acid Production Test Using Various Microorganisms

The microorganisms shown in Table 3 (all microorganisms were purchased from microorganism-distributing agencies; the distributors are described in the strain names) were subjected to preculture and microbial cell washing under the same conditions as in Example 1 except that each of ferulic acid, p-coumaric acid, benzoic acid, cis,cis-muconic acid, protocatechuic acid, and catechol was added to 2.5 mM as an inducer to the preculture medium. To 5 mL of the medium having the composition shown below, 0.5 mL of the washed suspension was added, and shake culture was performed at 30° C. for 48 hours.
10 g/L succinic acid
10 g/L glucose
10 g/L glycerol
1 g/L ammonium sulfate
50 mM potassium phosphate
0.025 g/L magnesium sulfate
0.0625 mg/L iron sulfate
2.7 mg/L manganese sulfate
0.33 mg/L calcium chloride
1.25 g/L sodium chloride
2.5 g/L Bacto tryptone
1.25 g/L yeast extract
pH 6.5.

The results of quantitative analysis of 3-hydroxyadipic acid accumulated in the culture supernatant are shown in Table 3. From these results, it was confirmed that all microorganisms have a capacity to produce 3-hydroxyadipic acid.

TABLE 3

| Test microorganism | 3-Hydroxyadipic acid production (mg/L) |
|---|---|
| *Acinetobacter radioresistens* NBRC102413 | 1.3 |
| *Acinetobacter baylyi* ATCC33305 | 1.2 |
| *Acinetobacter* sp. NBRC100985 | 1.5 |
| *Aerobacter cloacae* IAM1221 | 2.4 |
| *Alcaligenes faecalis* NBRC13111 | 7.1 |
| *Bacillus badius* ATCC 14574 | 8.2 |
| *Bacillus magaterium* IAM 1166 | 1.0 |
| *Bacillus roseus* IAM1257 | 1.5 |
| *Brevibacterium iodinum* NBRC3558 | 1.0 |
| *Corynebacterium acetoacidophilum* ATCC 21270 | 1.0 |
| *Corynebacterium acetoglutamicum* ATCC 15806 | 4.0 |
| *Corynebacterium ammoniagenes* NBRC12072 | 2.4 |
| *Corynebacterium ammoniagenes* NBRC12071 | 1.0 |
| *Corynebacterium glutamicum* ATCC 14020 | 1.9 |
| *Cupriavidus necator* DSM545 | 2.2 |
| *Cupriavidus metallidurans* NBRC101272 | 23 |
| *Cupriavidus necator* NBRC102504 | 3.4 |
| *Cupriavidus oxalaticus* NBRC13593 | 2.6 |
| *Cupriavidus* sp. NBRC102508 | 8.9 |
| *Delftia acidvorans* ATCC11299 | 4.1 |
| *Escherichia fergusonii* NBRC102419 | 2.5 |
| *Escherichia coli* NBRC12713 | 2.9 |
| *Hafnia alvei* ATCC 9760 | 6.7 |
| *Hafnia alvei* NBRC3731 | 13.3 |
| *Nocardioides albus* ATCC27980 | 1.7 |
| *Pseudomonas fluorescens* NBRC3081 | 7.4 |
| *Pseudomonas putida* NBRC12653 | 80.5 |
| *Pseudomonas putida* NBRC3738 | 18.9 |
| *Pseudomonas putida* ATCC17642 | 23.3 |
| *Pseudomonas putida* NBRC12996 | 40.7 |
| *Pseudomonas putida* ATCC15070 | 7.1 |
| *Pseudomonas putida* ATCC15175 | 6.6 |
| *Pseudomonas* sp. ATCC17472 | 11.4 |
| *Pseudomonas azotoformans* NBRC12693 | 48.4 |
| *Pseudomonas chlororaphis* subsp. *aureofaciens* NBRC3521 | 31.7 |
| *Pseudomonas chlororaphis* ATCC13985 | 1.4 |
| *Pseudomonas putida* ATCC8209 | 32.0 |
| *Pseudomonas putida* NBRC100650 | 16.3 |
| *Pseudomonas* sp. NBRC13302 | 15.9 |
| *Rhizobium radiobacter* IAM1526 | 1.6 |
| *Shimwellia blattae* NBRC105725 | 3.1 |
| *Sterptomyces vinaceus* NBRC13425 | 1.1 |
| *Streptomyces karnatakensis* NBRC13051 | 1.5 |
| *Streptomyces olivaceus* NBRC3409 | 1.8 |

Example 4

3-Hydroxyadipic Acid Production Test without Addition of Inducers

The microorganisms shown in Table 4 were subjected to preculture and microbial cell washing under the same conditions as in Example 3 except that the inducer used in Example 3 was not added. To 5 mL of the medium having the composition shown below, 0.5 mL of the washed suspension was added, and shake culture was performed at 30° C. for 48 hours.
10 g/L succinic acid
10 g/L glucose
1 g/L ammonium sulfate
50 mM potassium phosphate
0.025 g/L magnesium sulfate
0.0625 mg/L iron sulfate
2.7 mg/L manganese sulfate
0.33 mg/L calcium chloride
1.25 g/L sodium chloride
2.5 g/L Bacto tryptone
1.25 g/L yeast extract
pH 6.5.

The results of quantitative analysis of 3-hydroxyadipic acid in the culture supernatant are shown in Table 4.

From these results, it was confirmed that the microorganisms shown in Table 4 have a capacity to produce 3-hydroxyadipic acid even in cases where preculture is carried out without addition of an inducer.

TABLE 4

| Test microorganism | 3-Hydroxyadipic acid production (mg/L) |
|---|---|
| Alcaligenes faecalis NBRC13111 | 1.4 |
| Cupriavidus necator DSM545 | 1.2 |
| Escherichia coli NBRC12713 | 1.0 |
| Hafnia alvei NBRC3731 | 2.9 |
| Nocardioides albus ATCC27980 | 1.2 |
| Pseudomonas putida NBRC12653 | 4.4 |
| Pseudomonas putida NBRC3738 | 1.1 |
| Pseudomonas putida ATCC15175 | 2.4 |
| Pseudomonas putida ATCC8209 | 1.9 |
| Pseudomonas azotoformans NBRC12693 | 4.6 |
| Pseudomonas chlororaphis subsp. aureofaciens NBRC3521 | 1.9 |

Example 5

3-Hydroxyadipic Acid Production Test Using p-Coumaric Acid or Ferulic Acid as Inducer The microorganisms shown in Table 5 were subjected to preculture and microbial cell washing under the same conditions as in Example 4 except that p-coumaric acid or ferulic acid, among the substances added as inducers to the preculture medium in Example 3, was added to 0.5 mM. To 5 mL of the medium having the composition shown below, 0.5 mL of the washed suspension was added, and shake culture was performed at 30° C. for 48 hours. The results of quantitative analysis of 3-hydroxyadipic acid in the culture supernatant are shown in Table 5. From these results, it was found that the productivity of 3-hydroxyadipic acid can be increased even by addition of p-coumaric acid or ferulic acid alone as an inducer to the preculture medium compared to cases where neither of these is added.

TABLE 5

| Test microorganism | 3-Hydroxyadipic acid production (mg/L) | | |
|---|---|---|---|
| | No addition | p-coumaric acid added | Ferulic acid added |
| Alcaligenes faecalis NBRC13111 | 1.4 | 2.3 | 1.7 |
| Cupriavidus necator DSM545 | 1.2 | 2.9 | 2.6 |
| Escherichia coli NBRC12713 | 1.0 | 1.4 | 1.5 |
| Hafnia alvei NBRC3731 | 2.9 | 5.0 | 4.3 |
| Nocardioides albus ATCC27980 | 1.2 | 3.1 | 3.8 |
| Pseudomonas putida NBRC12653 | 4.4 | 6.9 | 7.6 |
| Pseudomonas putida NBRC3738 | 1.1 | 3.1 | 3.8 |
| Pseudomonas putida ATCC15175 | 2.4 | 7.6 | 5.2 |
| Pseudomonas putida ATCC8209 | 1.9 | 4.1 | 5.1 |
| Pseudomonas azotoformans NBRC12693 | 4.6 | 7.3 | 5.6 |
| Pseudomonas chlororaphis subsp. aureofaciens NBRC3521 | 1.9 | 4.3 | 4.0 |

INDUSTRIAL APPLICABILITY

By the present invention, 3-hydroxyadipic acid can be produced using a microorganism. The obtained 3-hydroxyadipic acid can be used as a raw material for polymers.

The invention claimed is:

1. A method of producing 3-hydroxyadipic acid, said method comprising the steps of:
   culturing in the presence of succinic acid at least one type of microorganism having a capacity to produce 3-hydroxyadipic acid, selected from the group consisting of microorganisms belonging to the genus *Escherichia*,
   wherein said microorganism(s) metabolize(s) succinic acid into 3-hydroxyadipic acid; and
   recovering the produced 3-hydroxyadipic acid.

2. The method according to claim 1, wherein said microorganism belonging to the genus *Escherichia* is *Escherichia fergusonii* or *Escherichia coli*.

3. The method according to claim 1, wherein said microorganism is cultured with a medium containing at least one inducer selected from the group consisting of ferulic acid, p-coumaric acid, benzoic acid, cis,cis-muconic acid, protocatechuic acid, and catechol.

* * * * *